United States Patent
Jaeggi

(10) Patent No.: US 10,502,751 B2
(45) Date of Patent: Dec. 10, 2019

(54) DEVICE FOR LIFTING A SAMPLE TUBE

(71) Applicant: Roche Diagnostics Operations, Inc., Indianapolis, IN (US)

(72) Inventor: Beat Jaeggi, Lucerne (CH)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 85 days.

(21) Appl. No.: 15/404,322

(22) Filed: Jan. 12, 2017

(65) Prior Publication Data
US 2017/0212139 A1   Jul. 27, 2017

(30) Foreign Application Priority Data

Jan. 22, 2016  (EP) .................................... 16152356

(51) Int. Cl.
*G01N 35/04*   (2006.01)
*G01N 35/00*   (2006.01)
(Continued)

(52) U.S. Cl.
CPC ............ *G01N 35/0099* (2013.01); *B01L 9/06* (2013.01); *B25J 15/0028* (2013.01); *B01L 9/50* (2013.01); *G01N 2035/0494* (2013.01)

(58) Field of Classification Search
CPC ............ G01N 2035/041; G01N 35/04; G01N 35/0099; B25J 15/0028; B25J 15/0038; B25J 15/0042; B25J 15/009; B25J 15/022; B25J 15/0253; B25J 15/026; B25J 15/0266; B25J 15/0273; B25J 15/028
See application file for complete search history.

(56) References Cited

U.S. PATENT DOCUMENTS 1,892,206 A   12/1932 Dietz
2,417,823 A   3/1947 Hodson et al.
(Continued)

FOREIGN PATENT DOCUMENTS

CN   2646101 Y   10/2004
CN   201133910 Y   10/2008
(Continued)

OTHER PUBLICATIONS

Extended European Search Report dated Jul. 15, 2016, in Application No. EP 16152356.8, 8 pages.

*Primary Examiner* — Justin N Olamit
(74) *Attorney, Agent, or Firm* — Roche Diagnostics Operations, Inc.

(57) ABSTRACT

A device for lifting a sample tube comprising a holder having holding elements for holding a sample tube is presented. The holder is supported moveably in the vertical direction between a lower holder position and an upper holder position for lifting and lowering a held sample tube. A centering tool having a pair of centering jaws extending parallel to one another in a longitudinal direction is provided. By moving the holder into the upper position, a held sample tube is lifted into a position between the centering jaws. The centering jaws are moveable to approach each other relative to the lifted sample tube for centering the lifted sample tube with respect to a vertical central axis. A sample handling device and to laboratory automation system comprising a device for lifting a sample tube and/or a sample handling device are also presented.

19 Claims, 3 Drawing Sheets

(51) Int. Cl.
*B25J 15/00* (2006.01)
*B01L 9/06* (2006.01)
*B01L 9/00* (2006.01)

(56) References Cited

U.S. PATENT DOCUMENTS

| | | | |
|---|---|---|---|
| 2,628,708 A | | 2/1953 | Wahl et al. |
| 3,036,624 A | | 5/1962 | Carter |
| 3,190,466 A | * | 6/1965 | Hostetler ............ B65G 57/303 414/788.8 |
| 4,596,107 A | | 6/1986 | Pfleger, Sr. |
| 5,078,057 A | | 1/1992 | Pearson |
| 5,297,668 A | | 3/1994 | Zink |
| 5,699,891 A | | 12/1997 | Gosdowski et al. |
| 5,765,675 A | | 6/1998 | Draghetti et al. |
| 5,800,780 A | | 9/1998 | Markin |
| 5,819,508 A | * | 10/1998 | Kraft .................. B67B 7/02 53/492 |
| 6,053,303 A | | 4/2000 | Wang |
| 6,056,106 A | | 5/2000 | van Dyke, Jr. et al. |
| 6,520,313 B1 | | 2/2003 | Kaarakainen et al. |
| 6,871,566 B2 | * | 3/2005 | Niwayama .......... B67B 7/182 53/381.4 |
| 7,152,504 B2 | | 12/2006 | Itoh |
| 8,083,994 B2 | | 12/2011 | Neeper et al. |
| 8,220,617 B2 | | 7/2012 | Eberle |
| 8,877,128 B2 | | 11/2014 | Fukugaki et al. |
| 8,973,736 B2 | | 3/2015 | Johns et al. |
| 9,000,360 B2 | | 4/2015 | DeWitte et al. |
| 9,063,103 B2 | | 6/2015 | Pedrazzini |
| 9,164,113 B2 | * | 10/2015 | Friedman ............ G01N 35/0099 |
| 9,248,982 B2 | | 2/2016 | Eberhardt et al. |
| 9,267,957 B2 | | 2/2016 | Haechler et al. |
| 9,321,621 B2 | | 4/2016 | Kitano et al. |
| 9,481,528 B2 | | 11/2016 | Pedrazzini |
| 9,527,233 B2 | | 12/2016 | Winzinger |
| 9,733,161 B2 | | 8/2017 | Nagai et al. |
| 9,910,054 B2 | | 3/2018 | Johns |
| 2006/0245865 A1 | | 11/2006 | Babson |
| 2007/0112399 A1 | * | 5/2007 | Baek .................... A61H 1/0292 607/90 |
| 2013/0233673 A1 | | 9/2013 | Itoh |
| 2013/0239527 A1 | * | 9/2013 | Clarke .............. B01L 3/50825 53/492 |
| 2014/0036276 A1 | * | 2/2014 | Gross ................ G01N 35/00732 356/614 |
| 2014/0342465 A1 | | 11/2014 | Haechler et al. |
| 2015/0177268 A1 | | 6/2015 | Reisch et al. |
| 2015/0233955 A1 | | 8/2015 | Nemoto et al. |
| 2017/0101272 A1 | | 4/2017 | Cherubini et al. |
| 2017/0212140 A1 | | 7/2017 | Ferihumer et al. |
| 2017/0212141 A1 | | 7/2017 | Schacher et al. |
| 2017/0350912 A1 | | 12/2017 | Maetzler et al. |

FOREIGN PATENT DOCUMENTS

| | | | |
|---|---|---|---|
| CN | 101309581 | | 11/2008 |
| CN | 102602697 A | | 7/2012 |
| CN | 204613223 U | | 9/2015 |
| EP | 2485058 A1 | | 8/2012 |
| EP | 2253960 B1 | | 5/2013 |
| EP | 2887071 A1 | | 6/2015 |
| GB | 797685 | | 7/1958 |
| JP | H07-234228 A | | 9/1995 |
| JP | 2004-223646 A | | 8/2004 |
| JP | WO 2014002953 A1 * | 1/2014 | ......... G01N 35/0099 |
| WO | 1983/000393 A1 | | 2/1983 |
| WO | 2011/138448 A1 | | 11/2011 |
| WO | 2014/147877 A1 | | 9/2014 |
| WO | 2015/059620 A1 | | 4/2015 |

* cited by examiner

DEVICE FOR LIFTING A SAMPLE TUBE

CROSS-REFERENCE TO RELATED APPLICATIONS

This application claims priority to EP 16152356.8, filed Jan. 22, 2016, which is hereby incorporated by reference.

BACKGROUND

The present disclosure relates to a device for lifting a sample tube for use in a laboratory automation system as well as to a sample handling device and to laboratory automation system comprising a device for lifting a sample tube and/or a sample handling device.

A laboratory automation system typically comprises a number of pre-analytical, analytical and/or post-analytical stations, in which samples such as, for example blood, saliva, swab, urine and other specimens taken from the human body, are processed. It is generally known to provide sample tubes containing the samples. The sample tubes are also referred to as test tubes. For processing of the sample, the sample tubes are distributed to designated stations or operating positions of the laboratory automation system.

Several sample tubes can be placed in racks for a handling. In an alternative distribution system, sample tubes are placed in an upright or vertical position in pucks having a retaining area for retaining one single sample tube.

For some pre-processing steps or processing steps, it is necessary to lift the sample tube from a transport or conveyance level. For example, a device for lifting and centering individual sample tubes in order to pierce a cap of a lifted sample tube or to enter an aspiration probe into the sample tube is known. A centering of the sample tube is achieved by passive chamfered surfaces provided at the device for piercing the cap or entering the aspiration probe.

However, there is a need for a device for lifting a sample tube allowing for a precise positioning of sample tubes at a lifted operating position that is simple in construction and robust in operation.

SUMMARY

According to the present disclosure, a device for lifting a sample tube is disclosed. The device can comprise a holder having holding elements for holding a sample tube. The holder can be supported moveably in the vertical direction between a lower holder position and an upper holder position for lifting and lowering a held sample tube. The device can also comprise a centering tool having a pair of centering jaws extending parallel to one another in a longitudinal direction. By moving the holder into the upper position, a held sample tube can be lifted into a position between the centering jaws. The centering jaws can be moveable to approach each other relative to the lifted sample tube for centering the lifted sample tube with respect to a vertical central axis.

Accordingly, it is a feature of the embodiments of the present disclosure to provide for a device for lifting a sample tube allowing for a precise positioning of sample tubes at a lifted operating position that is simple in construction and robust in operation. Other features of the embodiments of the present disclosure will be apparent in light of the description of the disclosure embodied herein.

BRIEF DESCRIPTION OF THE SEVERAL VIEWS OF THE DRAWINGS

The following detailed description of specific embodiments of the present disclosure can be best understood when read in conjunction with the following drawings, where like structure is indicated with like reference numerals and in which.

DETAILED DESCRIPTION

Figure 1:
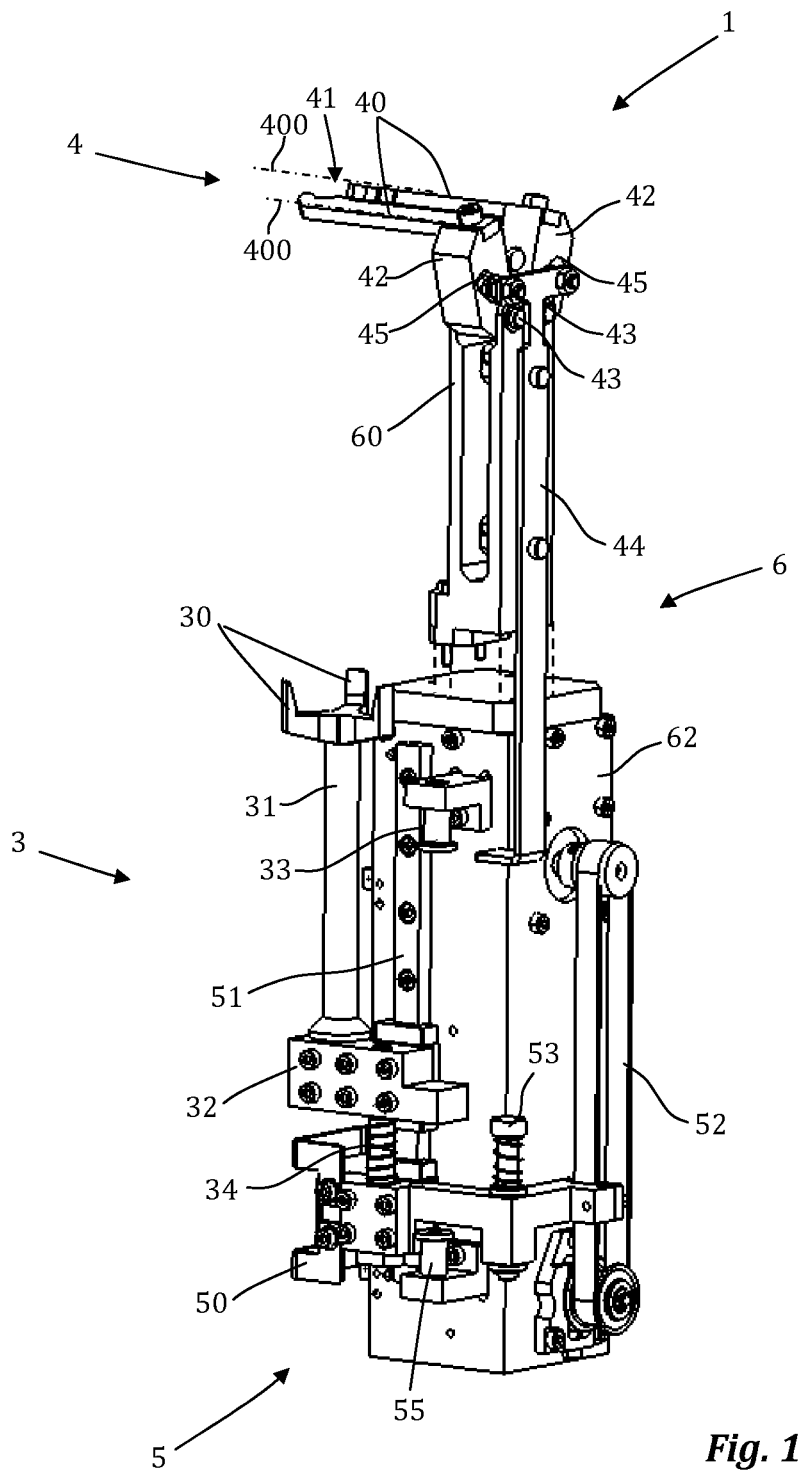
FIG. 1 illustrates a perspective view of a device for lifting sample tubes according to an embodiment of the present disclosure.

In the following detailed description of the embodiments, reference is made to the accompanying drawings that form a part hereof, and in which are shown by way of illustration, and not by way of limitation, specific embodiments in which the disclosure may be practiced. It is to be understood that other embodiments may be utilized and that logical, mechanical and electrical changes may be made without departing from the spirit and scope of the present disclosure.

A device for lifting a sample tube comprising a holder having holding elements for holding a sample tube is provided. The holder can be supported moveably in the vertical direction between a lower holder position and an upper holder position for lifting and lowering a held sample tube. The device can further comprise a centering tool having a pair of centering jaws extending parallel to one another in a longitudinal direction. By moving the holder into the upper position, a held sample tube can be lifted into a position between the centering jaws. The centering jaws can be moveable to approach each other relative to the lifted sample tube for centering the lifted sample tube with respect to a vertical central axis.

By closing the centering jaws, the sample tube can be centered with respect to vertical axis at least in the direction substantially perpendicular to the longitudinal direction of the centering jaws.

In one embodiment, the opposing surfaces of the centering jaws can be provided with recesses. The recesses, in one embodiment, can be V-shaped. In another embodiment, a recess in the form of a segment of a circle can be provided. The recess can allow the sample tubes during closing of the jaws to be centered in the direction substantially parallel to longitudinal direction of the centering jaws.

In one embodiment, the jaws can be moved in a substantially horizontal plane for approaching each other and to part from each other. In some embodiments, the jaws can be rigidly attached to a pair of pivotable tongs such as, for example, at about a 90° angle to a pair of pivotable tongs arranged in a vertical plane. The pivotable tongs can be pivotable about a substantially horizontal axis by applying a force in the vertical direction for causing the jaws to approach each other for centering the lifted sample tube with respect to the vertical central axis. Hence, for opening or closing the centering tool, the jaws can be moved along a circular path in the vertical and horizontal direction.

In some embodiments, one drive system can be provided. The holder can be moveable by the drive system at least from the lower holder position into the upper holder position. The centering jaws can be moveable by the drive system relative to the lifted sample tube for centering the lifted sample tube with respect to a vertical central axis. In one embodiment, the holder can be moved from the lower position into the upper position by the drive system and returned to the lower position by using gravitational forces and/or a return spring. In some embodiments, the to-and-fro movement of both the holder and the jaws can be caused by the drive system.

The drive system, in one embodiment, can comprise a first slide supported moveably in the vertical direction to-and-fro between a lower slide position and an upper slide position via a first intermediate slide position and second intermediate slide position. The first slide can interact with the holder for moving the holder from the lower holder position into the upper holder position upon movement between the lower slide position and the first intermediate slide position and can interact with the centering tool for actuating the centering tool upon movement between the second intermediate slide position and the upper slide position. The device can comprise a linkage system for converting a vertical movement of the first slide into a movement of the centering jaws towards and away from the lifted sample tube. In one embodiment, the second intermediate slide position can be closer to the lower position than the first intermediate slide position. The centering jaws can start to approach each other before the sample tube is in the final lifted position.

In some embodiments, the first intermediate slide position can coincide with the second intermediate slide position or can be below the second intermediate position so that upon the movement between the lower slide position and the coinciding intermediate position or the first intermediate position, the first slide can only interact with the holder for moving the holder from the lower holder position into the upper holder position and upon the movement between the coinciding intermediate position or the second intermediate position and the upper holder position, the first slide can only interact with the centering tool for actuating the centering tool.

In a laboratory automation system, sample tubes of different diameters can be processed. Therefore, a movement of the centering jaws can be chosen to allow for a sufficient closure of the jaws to center the sample tubes having a small diameter and to avoid damaging of sample tubes having a larger diameter. In one embodiment, a spring loaded pressure pin can be provided. The drive system can be drivingly coupled to the centering tool via the pressure pin and a motion transmission from the drive system to the centering tool can be interrupted upon reaching a limit force. Hence, upon reaching the limit force, the centering jaws can no longer be driven to approach each other, avoiding the damage of sample tubes having a larger diameter.

The drive system, in one embodiment, can comprise a belt drive for driving the first slide.

The holder can comprise, in some embodiments, a second slide supported moveably in the vertical direction. The first slide and the second slide can guide along a common guiding rail. The first slide and the second slide can be coupled by an elastically deformable element such as, for example, a spring element for a motion transmission. The elastically deformable element can allow for an interruption of the motion transmission in case a limit is reached. The first slide can be moved relative to the second slide with a deformation of the elastically deformable element. A restoration force can be chosen sufficiently large to avoid or limit a deformation when moving the holder from the lower position to the upper position under normal conditions.

A stop can be provided for limiting the upward movement of the holder. When the holder, in particular, the second slide, abuts the stop, a force larger than the restoration force can act on the elastically deformable element and the motion of the first slide may no longer be transmitted to the second slide.

The device, in some embodiments, can be arranged at least partly underneath a substantially horizontal plane in which the sample tubes can be conveyed. In one embodiment, the holder can comprise a column. The holding elements can be provided at the upper end of the column.

The device can be suitable for laboratory automation systems using sample tube carriers retaining one single sample tube, i.e., pucks. Therefore, in one embodiment, the holding elements can be adapted for holding a carrier adapted for retaining a single sample tube.

A sample handling device comprising at least one conveyor device for conveying a sample tube to an operating position in a substantially horizontal plane and a device for lifting the sample tube positioned at the operating position from the horizontal plane can be provided. The sample tube can be transferred while being placed in a puck to an operation position and lifted at the operating position, for example, for pipetting and/or for a handover of the sample tube to a second device. Various types of conveyor devices can be conceivable, for example a belt conveyor, a screw conveyor, a star wheel conveyor, a conveyor device comprising a transport plane and a number of electro-magnetic actuators being stationary arranged below the transport plane, wherein the electro-magnetic actuators can be adapted to move a sample tube carrier or combinations thereof.

A laboratory automation system with a number of pre-analytical, analytical and/or post-analytical stations and with a device for lifting a sample tube and/or with a sample handling device can be provided.

Figure 2:
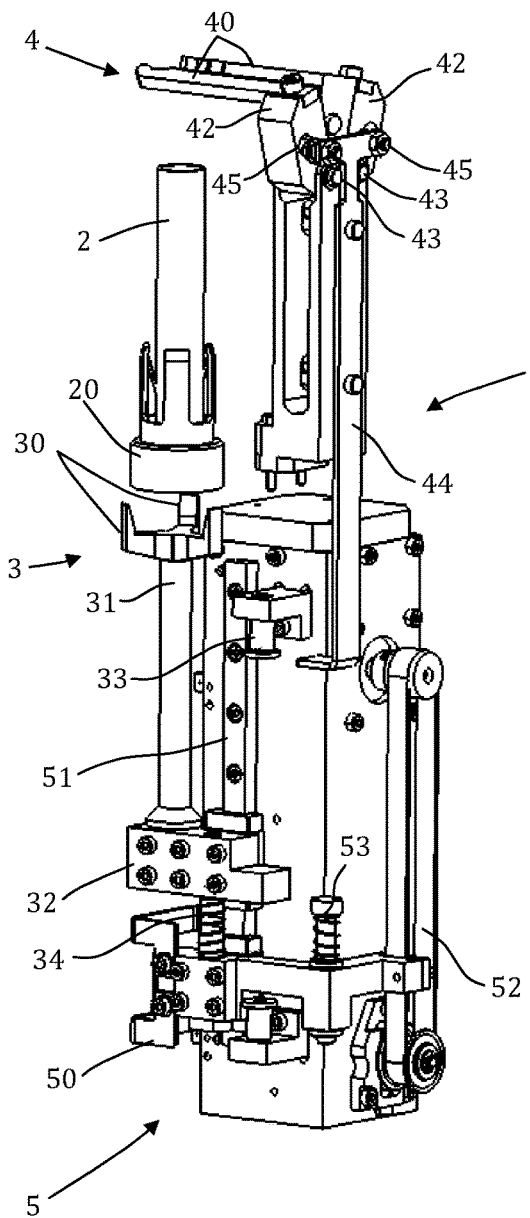
FIG. 2 illustrates a perspective view of the device of FIG. 1 with a sample tube before lifting the sample tube according to an embodiment of the present disclosure.

Referring initially to FIG. 1, FIG. 1 shows in a schematic perspective view a device 1 for lifting a sample tube 2 (see FIG. 2. not shown in FIG. 1). The device 1 can comprise a holder 3, a centering tool 4, a drive system 5 and pillar 6.

The pillar 6 can comprise an upper element 60 and a lower element 62, which can be connected fixed in position by a coupling element (indicated by broken lines in FIG. 1). The upper element 60 and the lower element 62, in one embodiment, can be connected fixed in position by a transport plane or a basis of a distribution system functioning as the coupling element. In other embodiments, the coupling element can function as a mounting component for the device 1. In still another embodiment, the upper element and the lower element can be one part.

The centering tool 4 can have a pair of centering jaws 40 extending substantially parallel to one another in a longitudinal direction 400. A sample tube placed between the centering jaws 40 can be centered with respect to a vertical central axis in the direction substantially perpendicular to the longitudinal direction 400 by moving the jaws 40 to approach each other, in other words by closing the centering jaws 40. The centering jaws 40 can be provided at opposing surfaces with recesses 41 allowing for a centering of a sample tube also in a direction substantially parallel to the longitudinal direction 400 of the centering jaws 40 upon closing the jaws 40.

The depicted centering tool 4 can further be provided with a linkage system comprising a pair of pivotable tongs 42 arranged in a vertical plane. Each pivotable tong 42 at one end at a pivot joint 43 can be mounted pivotable about a substantially horizontal axis to the upper element 60 of the pillar 6. The centering jaws 40 can be rigidly attached to the other ends of the pivotable tongs 42. The centering jaws 40 can extend from the pivotable tongs 43 with their substantially longitudinal direction 400 at about a 90° angle to the vertical plane. The linkage system can further comprise a rod 44 extending in the vertical direction and attached to the two tongs 42 at slotted holes 45. The rod 44 can be movable in the vertical direction relative to the upper element 60. In one embodiment, the upper element 60 can function as a guiding element for the rod 44. By moving the rod 44 upwards, the pivotable tongs 42 can be pivoted towards each other and the centering jaws 40 can also approach each other moving along a circular path for centering a sample tube arranged between the centering jaws 40.

The drive system 5 can comprise a first slide 50 slidingly mounted to the lower element 62 of the pillar 6 along a guide rail 51 and a belt drive 52 for driving the first slide 50. The first slide 50 can contact the rod 44 for a motion transmission via a spring loaded pressure pin 53 as will be explained in more detail below. A downward movement of the slide 50 can be limited by a stop 55.

The holder 3 can have holding elements 30 for holding a sample tube 2. In the depicted embodiment, the holding elements 30 can have three fingers offset by about 120°. A sample tube 2 can be retained in a sample tube carrier 20 (see FIG. 2), in which carrier 20 adapted for receiving one single sample tube 2 can be retained between the fingers.

The holder 3 can further comprise a second slide 32 and a column 31 arranged on the second slide 32. The holding elements 30 can be provided at the free upper end of the column 31. The second slide 32 can also be slidingly mounted to the lower element 62 of the pillar 6 along the guide rail 51. When moving the second slide 32 upwards, a sample tube 2 held by the holder 3, more particular by the holding elements 30, can be lifted into a position, in which the upper end of the sample tube can extend above the centering jaws 40 and a portion of the sample tube 2 can be arranged between the centering jaws 40. The upwards movement of the second slide 32 can be limited by a stop 33.

The second slide 32 can be coupled to the first slide 50 for a motion transmission via a spring element 34. The spring element 34, more particular its restoration force, can be configured such that initially upon moving the first slide 50 from a lower slide position shown in FIG. 1 upwards, the spring element 34 is not or only marginally deformed and the motion of the first slide 50 can be transferred to the second slide 32. When reaching the stop 33, the second slide 32 can be hindered from being moved further upwards, and unless the drive system 5 is stopped, the first slide 50 can be moved relative to the second slide 32 under deformation of the spring element 34.

Figure 3:
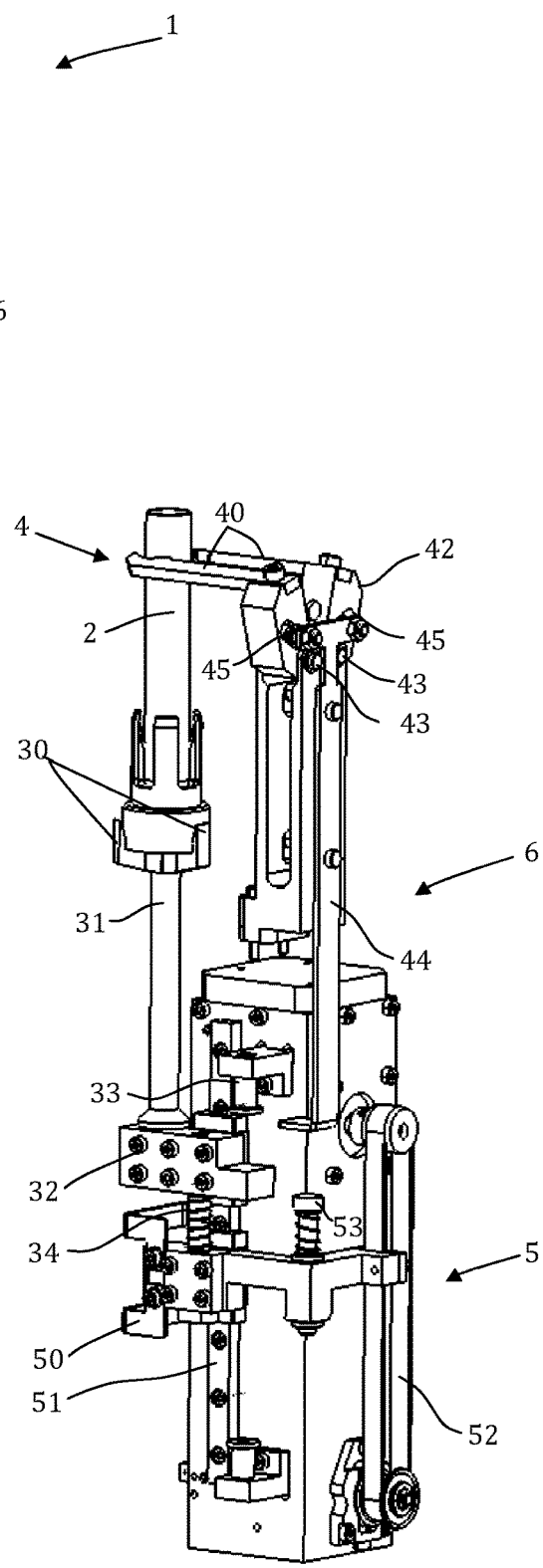
FIG. 3 illustrates a perspective view of the device of FIG. 1 with the sample tube during lifting of the sample tube according to an embodiment of the present disclosure.

The operation of the device 1 is explained in more detail in the following with reference to FIGS. 2 to 4.

As shown in FIG. 2, the sample tube 2 can be retained in a carrier 20 and positioned, for example, by a conveyor device above the holder 3. A support plate or the like (not shown in FIG. 2) can be provided for supporting the carrier 20 with the sample tube 2 in this position. For lifting the sample tube 2, the drive system 5 can be operated to move the first slide 50 from the lower slide position shown in FIG. 2 upwards. As shown in FIG. 3, the motion of the first slide 50 can be transferred to the second slide 32 and the sample tube 2 can be lifted such that its upper end can extend above the centering jaws 40 and a portion of the sample tube 2 can be positioned between the centering jaws 40.

Figure 4:
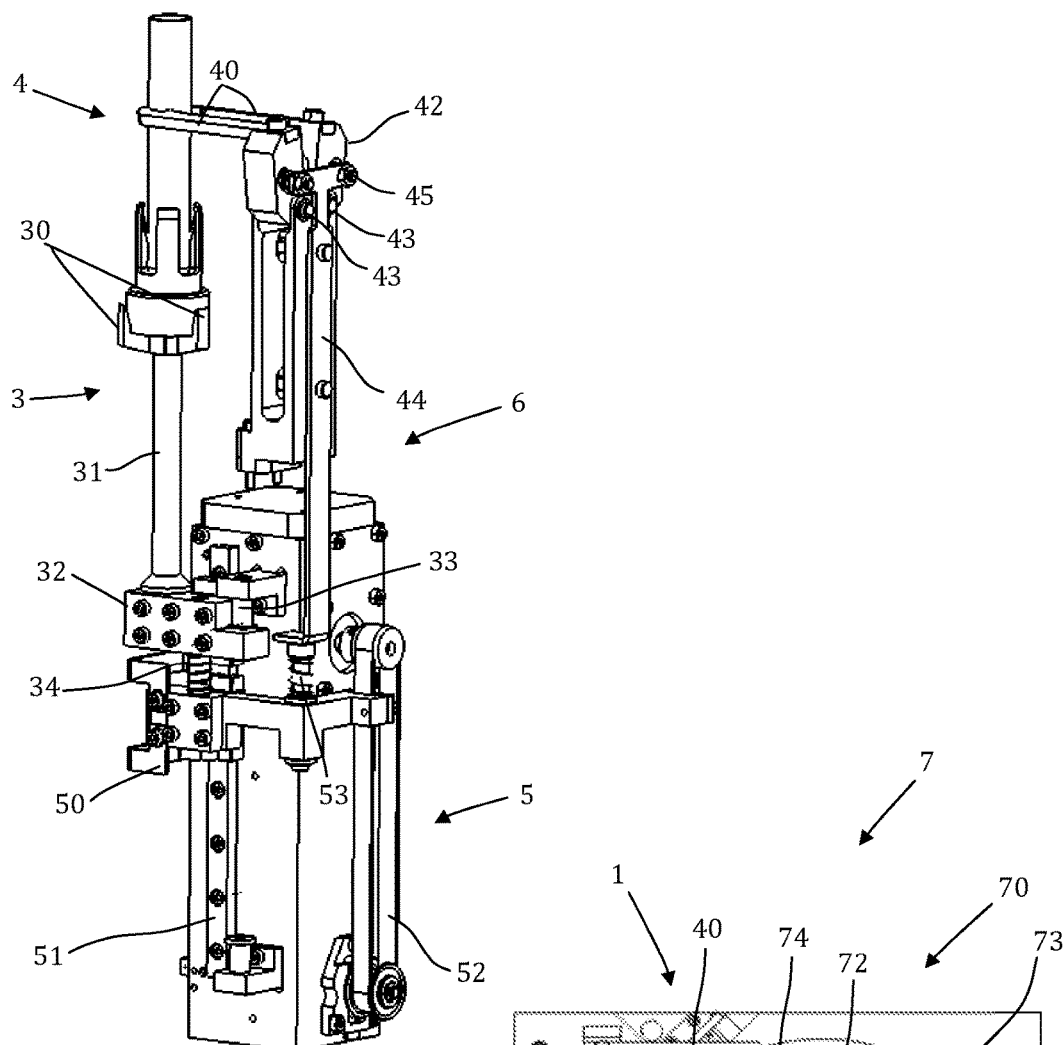
FIG. 4 illustrates a perspective view of the device of FIG. 1 with the sample tube during after lifting and centering of the sample tube according to an embodiment of the present disclosure.

When the second slide 32 reaches the stop 33, as shown in FIG. 4, the motion is no longer transferred to the second slide 32 and the spring element 34 can be compressed. The position of the first slide 50 when the second slide 32 reaches the limit stop 33 can be referred to as first intermediate slide position.

Further, in the upward movement, the first slide 50 can eventually contact the rod 44 via the pressure pin 53 and the motion of the first slide 50 can be transferred to the rod 44, thereby causing the centering jaws 40 to approach each other. The position of the first slide 50 when the pressure pin 53 contacts the rod 44 and the motion transmission to the centering tool 4 is started can be referred to as second intermediate slide position. The first and the second intermediate position may coincide.

Sample tubes 2 of different sizes, i.e. different diameters and different lengths can be handled. Therefore, in order to avoid damaging of the sample tubes 2 differing in the diameter when closing the jaws 40, the spring loaded pressure pin 53 can be provided. In the case of a counteracting force at the centering jaws 40 exceeds a threshold, the spring of the pressure pin 53 can be compressed and a motion transmission from the first slide 50 to the rod 44 can be stopped. Further, the distance between an upper end of the column 31 and, thus, a lower support area of the carrier 20 and the centering jaws 40 can be chosen in order to ensure that an upper end of short sample tubes 2 reaches a position in which it can be arranged between the centering jaws 40, when the second slide 32 reaches the limit stop 33. As can be seen in FIG. 4, a sample tube 2 having an average length can be contacted by the centering jaws 40 at a middle region upon centering.

Figure 5:
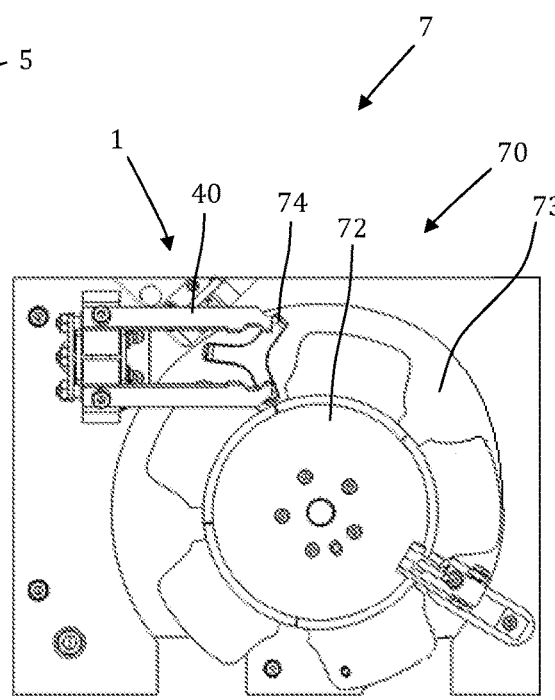
FIG. 5 illustrates a top view of a sample handling device comprising the device of FIG. 1 according to an embodiment of the present disclosure.

FIG. 5 is a top view of a sample handling device 7 comprising the device 1 shown in FIGS. 1 to 4. The sample handling device 7 shown in FIG. 5 can comprise a carousel 70, with a rotating disc 72. Carriers 20 (not shown in FIG. 5) retaining sample tubes 2 or empty carriers 20 can be conveyed to operating stations by a rotation of the disc 72. The holder 3 can be in the lower position arranged underneath, a supporting plate 73 of the conveyor over which the carriers 20 can be slidingly moved. As shown in FIG. 5, the supporting plate 73 can be provided with a cutout 74 allowing the holder 3 of the device 1 to contact the carrier 20 when moved upwards. The centering tool 4 with the centering jaws 40 can be arranged above the supporting plate 73.

In alternative, or in addition, to the carousel 70, the sample handling device 7, in one embodiment, can comprise a transport plane. A number of electro-magnetic actuators can be stationary arranged below the transport plane. The electro-magnetic actuators can be adapted to move a sample tube carrier 20 together with a sample tube 2 or while empty on top of the transport plane by applying a magnetic force to the sample tube carrier 20.

It is noted that terms like "preferably," "commonly," and "typically" are not utilized herein to limit the scope of the claimed embodiments or to imply that certain features are critical, essential, or even important to the structure or function of the claimed embodiments. Rather, these terms are merely intended to highlight alternative or additional features that may or may not be utilized in a particular embodiment of the present disclosure.

For the purposes of describing and defining the present disclosure, it is noted that the term "substantially" is utilized herein to represent the inherent degree of uncertainty that may be attributed to any quantitative comparison, value, measurement, or other representation. The term "substantially" is also utilized herein to represent the degree by which a quantitative representation may vary from a stated reference without resulting in a change in the basic function of the subject matter at issue.

Having described the present disclosure in detail and by reference to specific embodiments thereof, it will be apparent that modifications and variations are possible without departing from the scope of the disclosure defined in the appended claims. More specifically, although some aspects of the present disclosure are identified herein as preferred or particularly advantageous, it is contemplated that the present disclosure is not necessarily limited to these preferred aspects of the disclosure.

We claim:

1. A device for lifting a sample tube retained in a sample tube carrier, the device comprising:
   a holder having a column and fingers, wherein the fingers are provided at an upper end of the column and are configured to retain the sample tube carrier, wherein the holder is supported moveably in a vertical direction between a lower holder position and an upper holder position for lifting and lowering the sample tube carrier with a sample tube retained between the fingers;
   a centering tool having a pair of centering jaws extending parallel to one another in a longitudinal direction, wherein the centering jaws are arranged above the upper holder position such that by moving the holder into the upper position, a sample tube retained in a sample tube carrier retained between the fingers is lifted into a position between the centering jaws, and wherein the centering jaws are moveable to approach each other relative to the lifted sample tube for centering the lifted sample tube with respect to a vertical central axis; and
   one drive system, wherein the holder is moveable by the drive system at least from the lower holder position into the upper holder position and wherein the centering jaws are moveable by the drive system relative to the lifted sample tube for centering the lifted sample tube with respect to a vertical central axis; and
   a spring loaded pressure pin, wherein the one drive system is drivingly coupled to the centering tool via the pressure pin and a motion transmission from the one drive system to the centering tool is interrupted upon reaching a limit force.

2. The device according to claim 1, wherein the opposing surfaces of the centering jaws have recesses.

3. The device according to claim 1, wherein the centering jaws are rigidly attached to a pair of pivotable tongs arranged in a vertical plane.

4. The device according to claim 3, wherein the centering jaws are rigidly attached to the pair of pivotable tongs at a 90° angle.

5. The device according to claim 3, wherein a rod is attached to the pivotable tongs, wherein the pivotable tongs are pivotable about a horizontal axis by applying a force in the vertical direction to the rod causing the centering jaws to approach each other for centering the lifted sample tube with respect to the vertical central axis.

6. The device according to claim 1, further comprises, a stop for limiting an upward movement of the holder.

7. A sample handling device, the sample handling device comprising:
   at least one conveyor device for conveying a sample tube to an operating position in a horizontal plane; and
   a device according to claim 1 for lifting the sample tube positioned at the operating position from the horizontal plane.

8. A laboratory automation system, the laboratory automation system comprising:
   a number of pre-analytical, analytical and/or post-analytical stations; and
   a sample handling device according to claim 7.

9. A laboratory automation system, the laboratory automation system comprising:
   a number of pre-analytical, analytical and/or post-analytical stations;
   a device according to claim 1.

10. A device for lifting a sample tube retained in a sample tube carrier, the device comprising:
    a holder having a column and fingers, wherein the fingers are provided at an upper end of the column and are configured to retain the sample tube carrier, wherein the holder is supported moveably in a vertical direction between a lower holder position and an upper holder position for lifting and lowering the sample tube carrier with a sample tube retained between the fingers; and
    a centering tool having a pair of centering jaws extending parallel to one another in a longitudinal direction, wherein the centering jaws are arranged above the upper holder position such that by moving the holder into the upper position, a sample tube retained in a sample tube carrier retained between the fingers is lifted into a position between the centering jaws, and wherein the centering jaws are moveable to approach each other relative to the lifted sample tube for centering the lifted sample tube with respect to a vertical central axis; and
    one drive system, wherein the holder is moveable by the drive system at least from the lower holder position into the upper holder position, wherein the centering jaws are moveable by the drive system relative to the lifted sample tube for centering the lifted sample tube with respect to a vertical central axis, and, wherein the drive system comprises a first slide supported moveably in the vertical direction to-and-fro between a lower slide position and an upper slide position via a first intermediate slide position and second intermediate slide position, wherein the first slide interacts with the holder for moving the holder from the lower holder position into the upper holder position upon movement between the lower slide position and the first intermediate slide position and interacts with the centering tool for actuating the centering tool upon movement between the second intermediate slide position and the upper slide position.

11. The device according to claim 10, wherein the first intermediate slide position coincides with the second intermediate slide position or is below the second intermediate position so that upon the movement between the lower slide position and the coinciding intermediate position or the first intermediate position, the first slide only interacts with the holder for moving the holder from the lower holder position into the upper holder position, and upon the movement between the coinciding intermediate position or the second intermediate position and the upper holder position, the first slide interacts with the centering tool for actuating the centering tool.

12. The device according to claim 10, wherein the drive system comprises a belt drive for driving the first slide.

13. The device according to claim 10, wherein the holder comprises a second slide supported moveably in the vertical direction, wherein the first slide and the second slide guide along a common guiding rail.

14. The device according to claim 13, wherein the first slide and the second slide are coupled by an elastically deformable element for a motion transmission.

15. The device according to claim 14, wherein the elastically deformable element is a spring element.

16. The device according claim 10, further comprises,
a spring loaded pressure pin, where the drive system is drivingly coupled to the centering tool via the pressure pin and a motion transmission from the drive system to the centering tool is interrupted upon reaching a force limit.

17. A sample handling device, the sample handling device comprising:
at least one conveyor device for conveying a sample tube to an operating position in a horizontal plane; and
a device according to claim 10 for lifting the sample tube positioned at the operating position from the horizontal plane.

18. A laboratory automation system, the laboratory automation system comprising:
a number of pre-analytical, analytical, and/or post-analytical stations; and
a sample handling device according to claim 17.

19. A laboratory automation system, the laboratory automation system comprising:
a number of pre-analytical, analytical, and/or post-analytical stations; and
a device according to claim 10.

* * * * *